(12) United States Patent
Shekunov et al.

(10) Patent No.: US 7,208,106 B2
(45) Date of Patent: Apr. 24, 2007

(54) METHOD OF FORMING PARTICLES

(75) Inventors: Boris Y. Shekunov, Aurora, OH (US); Pratibhash Chattopadhyay, North Royalton, OH (US); Jeffrey S. Seitzinger, Broadview Heights, OH (US)

(73) Assignee: Ferro Corporation, Cleveland, OH (US)

( * ) Notice: Subject to any disclaimer, the term of this patent is extended or adjusted under 35 U.S.C. 154(b) by 0 days.

(21) Appl. No.: 10/536,330

(22) PCT Filed: Oct. 15, 2004

(86) PCT No.: PCT/US2004/034053

§ 371 (c)(1),
(2), (4) Date: Nov. 3, 2005

(87) PCT Pub. No.: WO2005/042219

PCT Pub. Date: May 12, 2005

(65) Prior Publication Data

US 2006/0138687 A1    Jun. 29, 2006

(51) Int. Cl.
B29B 9/00 (2006.01)

(52) U.S. Cl. .......................................................... 264/5

(58) Field of Classification Search ...................... None
See application file for complete search history.

(56) References Cited

U.S. PATENT DOCUMENTS

| 5,851,453 | A |   | 12/1998 | Hanna et al. |
|-----------|---|---|---------|--------------|
| 5,874,029 | A | * | 2/1999  | Subramaniam et al. ........ 264/12 |
| 5,922,253 | A |   | 7/1999  | Herbert et al. |
| 6,063,910 | A | * | 5/2000  | Debenedetti et al. ........ 530/418 |
| 6,153,129 | A |   | 11/2000 | Herbert et al. |
| 6,358,443 | B1 |  | 3/2002  | Herbert et al. |
| 6,562,952 | B1| * | 5/2003  | Rajewski et al. ........... 530/418 |

\* cited by examiner

*Primary Examiner*—Mary Lynn Theisen
(74) *Attorney, Agent, or Firm*—Rankin, Hill, Porter & Clark LLP

(57) ABSTRACT

The present invention provides a method of forming particles that involves contacting a solution, which includes a solute and/or other material to be precipitated dissolved or dispersed in a solvent, with a first compressed or liquefied gas at an initial temperature to form a mixture. The mixture is then expanded at a first temperature to form droplets. Depending upon the composition of the droplets and the first temperature, the droplets may be in a solid state or a liquid state. The droplets are then contacted with an extracting fluid at a second temperature to extract the solvent from the droplets. The method can be used to produce micro and nanoparticles suitable for various drug delivery systems.

20 Claims, 12 Drawing Sheets

METHOD OF FORMING PARTICLES

BACKGROUND OF THE INVENTION

1. Field of Invention

The present invention relates to a method of forming particles. More particularly, the present invention relates to a method of forming particles that involves contacting a solution and a compressed or liquefied gas together at an initial temperature to form a mixture, expanding the mixture at a first temperature to form droplets, and then contacting the droplets and an extracting fluid together at a second temperature to extract solvent from the droplets and thereby obtain particles.

2. Description of Related Art

The majority of particles used in the pharmaceutical industry are produced on a large scale using such techniques as crystallization, precipitation, milling and spray drying. Thermally labile materials are often particulated by techniques such as lyophilization, spray freezing and vacuum drying. Particles can be formed in other ways, such as by phase separation/coacervation, emulsion, high pressure homogenization and supercritical fluid precipitation methods. These various known methods can be used to produce particles in some instances, but there are certain limitations.

Solvent-based methods typically involve precipitation of a solute material from aqueous or organic solutions using anti-solvents (non-solvents). These methods can be practiced on a large industrial scale, but there are inherent problems with the control of particle size distribution and particle morphology. It is particularly difficult to obtain uniform particles having diameters in the lower micron and submicron size range using conventional solvent-based methods. Moreover, solvent-based methods require secondary processes such as filtration, drying, granulation and micronization in order to obtain fine powders from the precipitated product. Another disadvantage of solvent-based methods is that it is usually not possible to engineer particular particles such as, for example, porous, hollow or coated particles, microspheres, and microcapsules. Moreover, there are also significant problems associated with residual solvent in the final product, and with variations between crystallinity and purity from batch to batch.

Milling, mechanical grinding or other mechanical micronization techniques are commonly used to process materials into micro and nanoparticles for oral, respiratory and injectable formulations. These processes can be time-consuming and are generally unsuitable for particulating soft and ductile organic pharmaceuticals. Moreover, since the size distribution of particles processed using these techniques tends to be broad, only a small fraction of the particles produced are in the desired size range after several hours of processing. In addition, the shear forces and temperature generated in milling can produce uncontrollable variations of the solid-state structure of the particles, which may render the formulations unstable or ineffective.

The spray drying technique involves the evaporation of volatile solvents at elevated temperatures, typically between 100° C. and 200° C., using fine nozzles. Although spray drying can be used to produce substantially spherical microparticles, which may be porous or hollow for specific formulations, this technique is problematic for the processing of sensitive or thermally labile materials and crystalline materials. Contact with organic solvents and/or exposure to elevated temperatures can denature some biological materials such as proteins and peptides during processing. Moreover, it is difficult to produce and collect particles having diameters in the submicron range, which results in decreased product yield.

A well-known process for making dry solid formulations of a biomaterial or a thermally labile material is lyophilization. This technique involves freeze-drying, typically of an aqueous solution of the material using high vacuum. Unfortunately this process is very expensive and cannot directly produce particles in the narrow micro—or nanometer size range required for many drug delivery systems.

Another method that suitable for production of particles of thermally labile materials is spray freeze-drying. In this method a solution containing a sensitive material such as a protein, for example, and an excipient is sprayed into a low-temperature liquid, typically liquid nitrogen to form frozen droplets. The frozen droplets are then subsequently lyophilized in order to obtain the particles. Such a process is disclosed in U.S. Pat. No. 6,284,282, which is hereby incorporated by reference in its entirety. However, the low temperature of liquid nitrogen and the corresponding abrupt decrease of temperature or thermal shock during the spraying can degrade some proteins, peptides and other biologically active materials. This can be especially problematic when the spray results in the generation of small particles having a large specific surface area. In addition, the current spray-freezing processes have significant economic disadvantages for large scale-reduction related to handling the liquid nitrogen and excessive costs involved in the second lyophilization stage.

A method that involves spray-freezing a solution into a liquid solvent with consequent liquid-liquid extraction to produce drug-polymer particles is described in U.S. Pat. No. 5,019,400, which is hereby incorporated by reference in its entirety. In this method a solution containing an active material and a polymer is sprayed into a liquid non-solvent such as ethanol or layer of inert liquefied gas such as liquid nitrogen overlaying the layer of frozen liquid non-solvent. The frozen solution droplets undergo liquid-liquid extraction during a thawing cycle involving the droplets and the liquid non-solvent. The inert liquefied gas is then evaporated after freezing of droplets of polymer solution. The major disadvantage of this method is related to the residual solvent left in the product after extraction, which requires a separate filtering of particles, washing and consequent vacuum-evaporation or other purification stages. In addition, the method disclosed is only suitable for the production of relatively large particles with size of tens of micrometers, due to low dispersion efficiency of ultrasonic or gas-blowing nozzles.

A method that involves spray-freezing a solution into a freezing zone created by a spray of liquid nitrogen or other liquefied gas such as liquid argon and helium with an initial temperature sufficiently low to freeze the solution droplets is described in U.S. Pat. No. 6,358,443, which is hereby incorporated by reference in its entirety. Similar to the previously discussed technique, this method has a disadvantage of handling liquefied low temperature gases on large scale. Additional problems include the unwanted incorporation of residual solvent in the resulting particles, and the inability to produce small particles (i.e., having diameters less than tens of micrometers) due to the low dispersion efficiency of the nozzles used.

Vacuum-assisted freezing is another process for the preparation of small particles of temperature-sensitive compounds. In vacuum-assisted freezing, a solution is introduced into an evacuated chamber in the form of a spray. Droplets of the spray are at a sufficiently low temperature to freeze at the vacuum pressure inside the chamber. The frozen solvent is sublimated from the collected frozen droplets. Such a procedure is disclosed in U.S. Pat. No. 5,727,333, which is hereby incorporated by reference in its entirety. Unfortunately, the requirement of a vacuum limits the throughput of the solution and prevents control over the particle size, in particular, for particles in the lower micron size range. Furthermore, the cost of the process is similar to or higher than the cost of the lyophilization process. All these factors hinder the industrial applicability of this process.

Methods involving supercritical fluid (SCF) precipitation facilitate particle formation at near-ambient temperatures and eliminate a need for a liquid-vapor interface. However, SCF precipitation has disadvantages because water and carbon dioxide ($CO_2$) are poorly miscible fluids, and therefore any precipitation technique using $CO_2$ and an aqueous solution requires the addition of an organic co-solvent to increase the solubility of water in $CO_2$. Many biologically active materials are irreversibly degraded as a result of contacting the organic co-solvent. Precipitation of uniform size particles for certain materials is difficult using supercritical fluids because of the same limitations as for the liquid solution precipitation process. And, SCF methods involve high-pressure equipment and therefore involve relatively high capital and running costs.

For the reasons thus stated, there exists a need for a particle production technique that would be capable of processing different drug and excipient materials, including thermally labile, water-soluble or water insoluble substances, into micro and nanoparticles, particles of respiratory size range (1–5 μm), porous particles, and/or composite drug-excipient particles. Such a technique would preferably exhibit sufficient processing efficiency to be economically suitable for use in the large-scale industrial production of particles. Further, it would be advantageous for such a technique to offer flexibility in terms of particle solid-state properties such as size and morphology.

BRIEF SUMMARY OF THE INVENTION

The present invention provides a method of forming particles that involves contacting a solution and a first compressed or liquefied gas together at an initial temperature to form a mixture, expanding the mixture at a first temperature to form droplets, and then contacting the droplets and an extracting fluid together at a second temperature to extract solvent from the droplets and thereby obtain particles, and the apparatus used to produce such particles. According to the invention, the solution, which comprises a solute and/or other material to be precipitated dissolved or dispersed in a solvent, is contacted with the first compressed or liquefied gas at an initial temperature to form a mixture. The solution and first compressed or liquefied gas are preferably contacted together in a heated nozzle. The mixture is expanded at a first temperature to form droplets. Depending upon the composition of the droplets and the first temperature, the droplets may be in a solid state or a liquid state. The droplets are then contacted with an extracting fluid at a second temperature to extract the solvent from the droplets. Extraction can be by solid-liquid or liquid-liquid extraction, depending upon whether the droplets are frozen (either upon expansion or upon contact with the extracting fluid) or simply cooled. The extracting fluid is preferably a homogeneous mixture of a second compressed or liquefied gas and a co-solvent, which are miscible with each other. If the droplets are in a liquid state while in contact with the extracting fluid, the extraction of the solvent from the liquid droplets results in the precipitation of the solute and/or other materials present in the solution. An additional amount of the second compressed or liquefied gas can be added at a third higher temperature above the critical temperature of the gas to remove both the solvent and co-solvent.

The method can be used to produce micro and nanoparticles suitable for various drug delivery systems such as, for example, particles for pulmonary or respiratory drug delivery systems using dry-powder inhalers (DPI) or metered dose inhalers (MDI) as well as production of amorphous and crystalline particles for oral or parenteral drug delivery. The process provides high yields of uniform particles having both controllable and reproducible particle size and morphology. The process can be used to process biologically active agents such as proteins, monoclonal antibodies, peptides, nucleic acids, polysaccharides, steroids, antibiotics, anesthetics, sedatives, cardiovascular agents, anti-tumor agents, vitamins, organic and inorganic drugs and diagnostic agents into small particles.

The foregoing and other features of the invention are hereinafter more fully described and particularly pointed out in the claims, the following description setting forth in detail certain illustrative embodiments of the invention, these being indicative, however, of but a few of the various ways in which the principles of the present invention may be employed.

DETAILED DESCRIPTION OF THE INVENTION

The present invention provides a method and apparatus for producing particles having a substantially uniform diameter that is within the range of from about $10^{-8}$ to about $10^{-2}$ m. Accordingly, the method of the invention can be used to produce nanoparticles, which are hereby defined as particles having an average diameter within the range of from about $10^{-8}$ to about $10^{-6}$ m, respirable particles, which are hereby defined as particles having an average diameter within the range of from about $10^{-7}$ to about $10^{-5}$ m, and injectable particles (i.e., particles suitable for intravenous, subcutaneous, intramuscular or other types of injections), which are hereby defined as particles having an average diameter within the range of from about $10^{-7}$ to about $10^{-4}$ m. Materials that can be formed into particles in accordance with the invention include, for example, proteins, peptides, biological molecules, water-soluble drugs, water-insoluble drugs, steroids, antibiotics, small molecule drugs, pro-drugs, polymers, lipids, sugars, polysaccharides, excipients, stabilizers, salts, buffers. The particles formed can comprise a single biologically active material or may comprise a plurality of compounds and/or materials. The method of the invention can be used to form particles that are dispersed or encapsulated within other materials to form composites, which allow for controlled, sustained, extended, delayed release and/or targeted drug release. Particles formed in accordance with the method of the invention may also be hollow or porous, which can be advantageous, for example, for preparing compositions for respiratory drug delivery.

Figure 1:
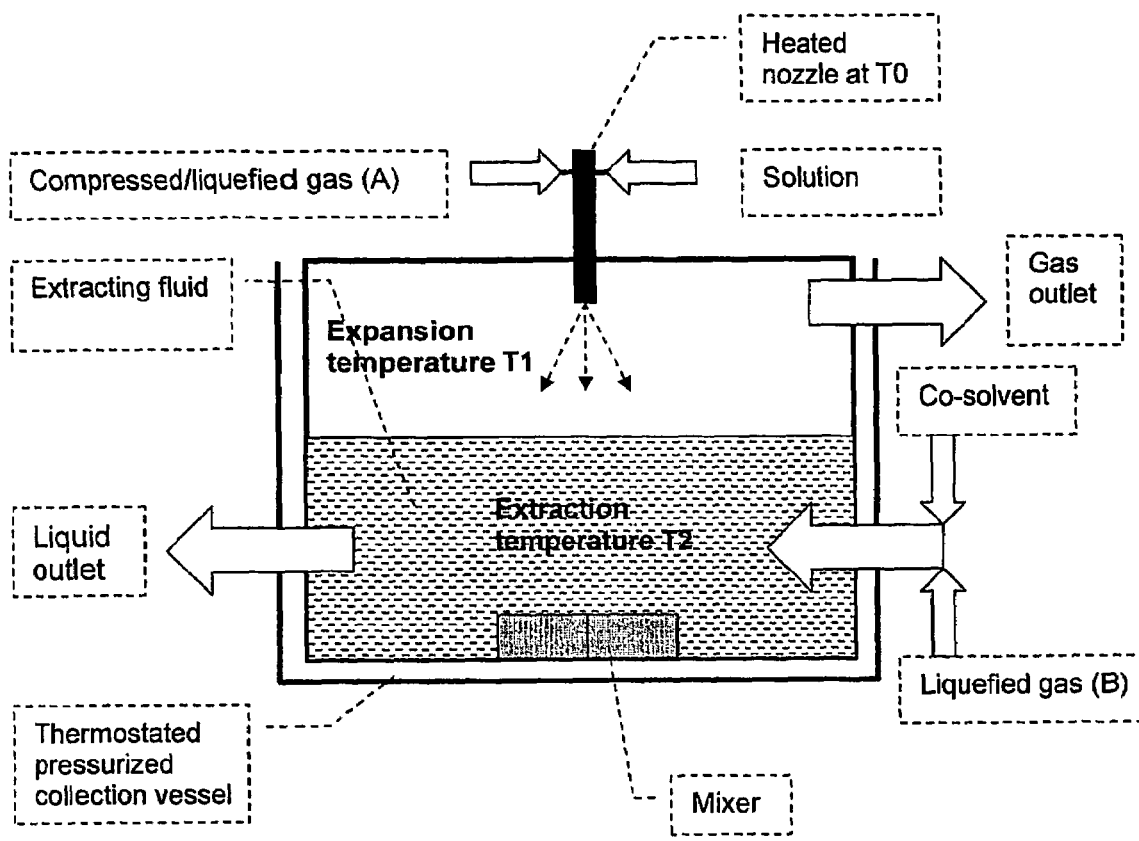
FIG. 1 is a schematic representation of an apparatus for use in producing particles in accordance with the present method.

FIG. 1 shows a schematic representation of an apparatus suitable for use in practicing the method of the invention. The apparatus includes a collection-extraction vessel equipped with a pressurizable collection-extraction chamber, a thermostat, a cooling and/or heating device, a heated spray nozzle and a mixer. A solution comprising a solute and/or other materials dissolved in or dispersed in one or more solvents, is preferably contacted with a first compressed or liquefied gas in a nozzle to form a mixture. The solution and the first compressed or liquefied gas can be supplied to the nozzle using metering pumps. The solution and first compressed or liquefied gas exit the nozzle and expand to a first temperature. Expansion of the compressed or liquefied gas results in the formation of droplets and substantial cooling due to the Joules-Thompson effect. If the first temperature is below the freezing point of the solution, the droplets will freeze and thus be in a solid state. If the first temperature is higher than the freezing point of the droplets, the droplets will remain in a liquid state, but will be substantially cooled.

After exiting the nozzle, the droplets contact an extracting fluid, which can be supplied to the chamber using metering pumps. The extracting fluid preferably comprises a miscible blend of a second compressed or liquefied gas and a co-solvent. The collection-extraction vessel is also preferably equipped with an outlet for removing the extracting fluid and the solvent extracted from the droplets.

The collection-extraction vessel is preferably cylindrical, but other shapes can be used. The vessel must be able to withstand the pressure of liquefied and compressed gases at the processing temperatures. The collection-extraction vessel should be placed into a cooling jacket, which allows for regulation and adjustment of the temperature of the collection-extraction chamber. In a preferred apparatus, the cooling jacket is in fluid communication with a cooling device such as, for example, a liquid-gas circulating bath or an electrically cooled heat exchanger. A separate heating conduit should also be installed to allow for heating of the vessel, if required. The cooling, heating and isolation devices can be controlled using a thermostat, as shown in FIG. 1.

The collection-extraction vessel is preferably equipped with a mechanical agitator and a filter. The filter is disposed inside the vessel in order to prevent particles from escaping the vessel during continuous mode processing. It will be appreciated that a filter is optional when particles are processed in a batch mode. The mechanical agitator is positioned inside the collection-extraction chamber to provide a means of mixing the contents of the collection-extraction vessel and also to aid in maintaining isothermal conditions throughout the vessel.

The solution containing the material to be particulated is injected into the collection-extraction chamber using a spray nozzle. The nozzle is preferably a two-component expansion nozzle, such as impinging nozzle or internal and external air-blast atomizers, which allow for fast mixing of the solution and liquefied gas as shown in FIG. 1. The nozzle aids in the atomization process and also cause the gas stream to expand and cool because of the well-known Joule-Thomson effect. Other suitable nozzles and atomizers that can be employed to assist the atomization process include: rotary atomizers, ultrasonic atomizers or nozzles, coaxial nozzles, capillary silica tubes (single or multiple), and frits. The spray nozzle is heated to prevent nozzle clogging.

Figure 2:
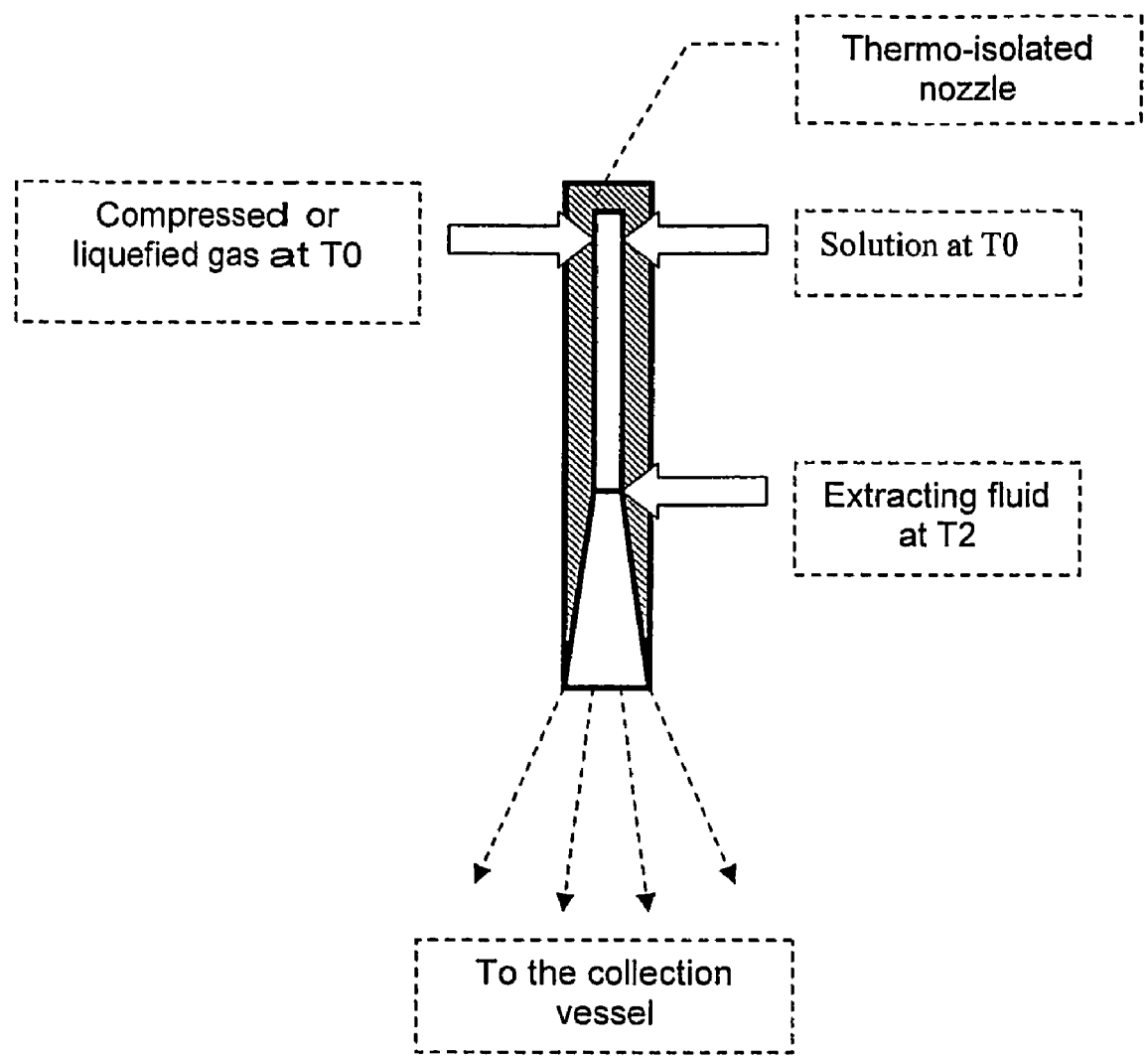
FIG. 2 is a schematic representation of a nozzle assembly that can be used in the apparatus shown in FIG. 1.

A convenient design of the nozzle suitable for this invention is shown in FIG. 2. The upper part of the nozzle is design to dispersed solution with a first compressed or liquefied gas at initial temperature, sometimes hereinafter referred to as "T0". During expansion at a first temperature, sometimes hereinafter referred to as "T1", the droplets thereby formed contact an extracting fluid, which preferably comprises a second compressed or liquefied gas and a miscible co-solvent. The nozzle shown in FIG. 2 provides uniform and continuous mixing between the solution and the first compressed or liquefied gas, and uniform and continuous mixing and cooling between the solution and the extracting fluid.

Figure 3:
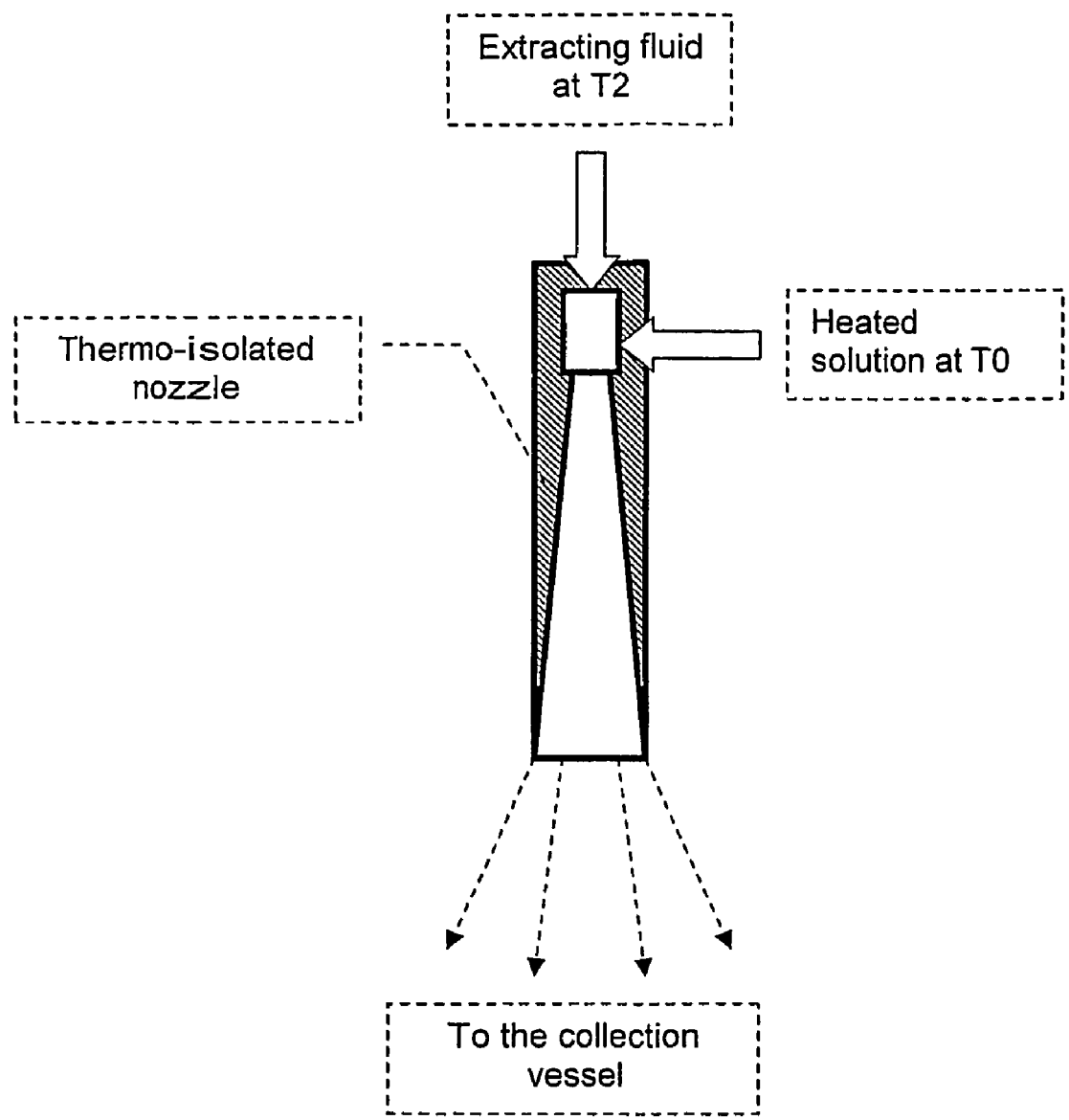
FIG. 3 is a schematic representation of an alternative nozzle assembly that can be used in the apparatus shown in FIG. 1.

FIG. 3 shows an alternative nozzle configuration that facilitates inline mixing between the solution and extracting fluid. It will be appreciated that the addition of an energizing gas, such as compressed nitrogen or air, to each of the streams will create mixing between droplets of the solution and extracting fluid leading to first, freezing and then extraction of the solvent by extracting fluid. Freezing is faster than extraction because thermal conductivity is significantly greater than diffusivity in the liquid or liquefied media. The nozzles can be heated using integral heating elements or using externally applied heating means, if necessary. Separate cooling elements such as cooling heat exchangers, adiabatic coolers and other suitable elements known from the arts can be used to cool the extracting fluid before it enters the nozzle.

Figure 4:
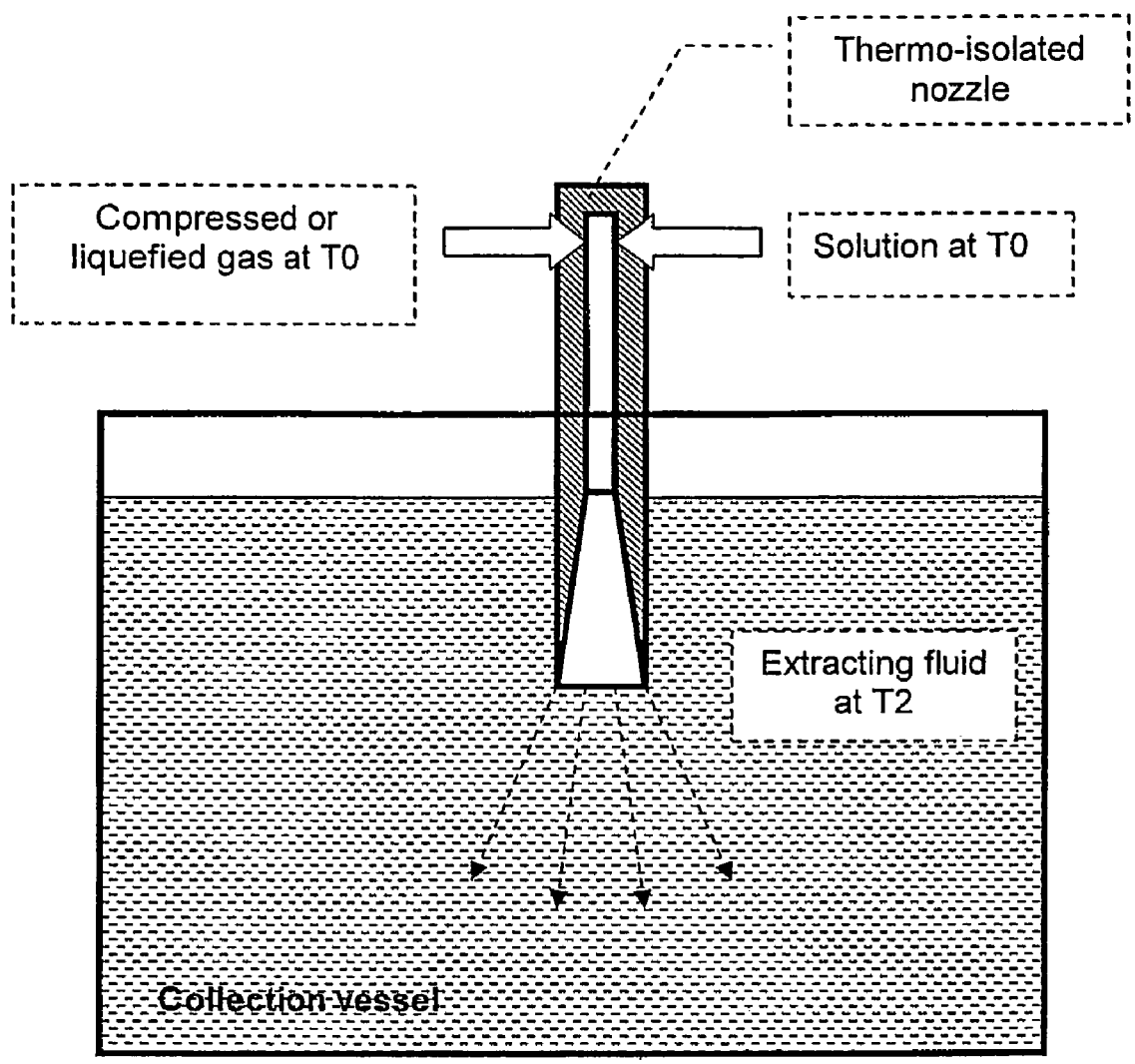
FIG. 4 is a schematic representation of a nozzle configured for immersion into an extracting fluid.

The nozzle can be placed above the surface of extracting fluid or inserted below the surface of the extracting fluid to provide different regime of the freezing process and different particle morphology. An example of nozzle configured for immersion into the extracting fluid is shown in FIG. 4. The nozzle is isolated from the extracting fluid by a thermal jacket, which is preferably made of polytetrafluoroethylene (PTFE) or other substantially inert material. The continuous flow of heated solution and optionally, the flow of compressed gas, creates a jet inside the extracting fluid, which prevents nozzle blockage.

The first compressed or liquefied gas is preferably selected from the group consisting of carbon dioxide, nitrogen, propane, ethane, nitrogen oxide, ammonia, hydrofluorocarbons and other gases that exhibit a significant Joule-Thomson effect, which is required for cooling and high expansion coefficient required for efficient dispersion. The solution mixed with the first compressed or liquefied gas preferably comprises a solute dissolved or dispersed in a solvent. Thus, the solution can comprise a dispersion or an emulsion.

Preferred solvents for use in the invention include, for example, water, alcohol, toluene, ethyl acetate, methylene chloride, chloroform, dimethyl sulfoxide (DMSO), dimethyl formamide (DMF), tetrahydrofuran (THF), other organic or inorganic solvents, and combinations thereof selected on the basis of their chemical inertness and sufficient solubility power/dispersability for the solute. In addition the freezing point of the solution should be in the vicinity of the expansion and extraction temperatures, as is explained in greater detail below in the Methods section.

The solute is preferably a biologically active material, for example, a drug or a pro-drug, a pharmaceutical, or a therapeutic agent. Alternatively, the solute can be, for example, a medicinal agent, sugar, pigment, toxin, insecticide, viral material, diagnostic aid, agricultural chemical, nutritional material, protein, alkyloid, alkaloid, peptide, animal and/or plant extract, dye, explosive, paint, polymer precursor, cosmetic, antigen, enzyme, catalyst, nucleic acid, zeolite, polymer precursor, and combinations thereof. The solute can include an additional material, for example, a carrier, polymer, filler, disintegrant, binder, solubilizer, excipient, and combinations thereof. Solute may also comprise a polymer. Suitable polymers include, for example, polysaccharides, polyesters, polyethers, polyanhydrides, polyglycolides (PLGA), polylactic acids (PLA), polycaprolactones (PCL), polyethylene glycols (PEG), and polypeptides.

Surfactants, agents, buffers, emulsifiers, or other modifiers can be added to the solution, as desired, to affect the precipitation mechanism of the solute from the solution during extraction. Preferred surfactants for use in the invention include non-ionic, anionic and cationic surfactants. Preferred emulsifiers include biodegradable surfactants such as TWEEN, lethicin and also poly(vinyl pyrrolidone), polyglycerol, polyricinoleate, poly(vinyl alcohol), and block copolymers. As noted above, the solution according to the present invention can be in the form of an emulsion, colloidal suspension, or a combination thereof, for which surfactants may be necessary.

The extracting fluid preferably comprises a homogeneous mixture of a second compressed or liquefied gas and co-solvent that is miscible with the second compressed or liquefied gas to form a single phase liquid. The second compressed or liquefied gas in the extracting fluid is preferably selected from the group consisting of carbon dioxide, propane, ethane, nitrogen oxide, ammonia, hydrofluorocarbons, and other gases that are miscible with or highly soluble in the solvents and co-solvents used. Carbon dioxide, $CO_2$, is the most preferred compressed or liquefied gas, both for use as the first compressed or liquefied gas for use as the second compressed or liquefied gas.

The co-solvent(s) used in the extracting fluid are preferably selected from the group consisting of ethanol, alcohol group, acetone, pentane, isopentane, ethyl acetate, methylene chloride, chloroform, dimethyl sulfoxide (DMSO), dimethyl formamide (DMF), tetrahydrofuran (THF), water, other organic or inorganic solvents, and combinations thereof. These co-solvents are selected: first, on the basis of their miscibility with the second compressed or liquefied gas; second, based on their miscibility and or high solubility with the solvent used in solution; third, on being non-solvents (anti-solvents) at the extracting temperature for the solute; and fourth, on the basis of maintaining the freezing point of the extracting fluid at a temperature that is lower or about the same as the freezing point of the solution, which allows for the solid-liquid or liquid-liquid extraction of the solvent, as is more thoroughly described in the Methods section below. The weight ratio of the second compressed or liquefied gas to co-solvent can be within the range of from 0:100 to 100:0, depending on the required rate of extraction and the magnitude of the extraction temperature.

The solution and the co-solvent can be effectively pumped using high-pressure liquid chromatography (HPLC) reciprocating pumps, such as the model PU-1586, which is commercially available from Jasco Inc. (Easton, Md.). Suitable alternative pumps include syringe pumps, such as the 1000D or 260D pumps, which are commercially available from Isco Inc. (Lincoln, Nebr.). Other alternatives are diaphragm or plunger high-pressure pumps available form Milton Roy (France).

The first and second compressed or liquefied gases can be effectively pumped using a P-200 high-pressure reciprocating pump commercially available from Thar Technologies, Inc. (Pittsburgh, Pa.). Suitable alternative pumps include diaphragm pumps and air-actuated pumps that provide a continuous flow of fluid.

Preferably suitable mixing means are employed in the collection-extraction chamber for mixing the solution droplets and the extracting fluid. The mixing devices that can be employed for effective mixing include: mechanical agitators, magnetic stirrers and ultrasonic baths. Increased mixing reduces the likelihood of the formation of heated zones inside the vessel and also improves the mass transfer rates between the solvent droplets and the extracting fluid.

The collection-extraction vessel is preferably equipped with a backpressure regulator (BPR) and a safety valve. The BPR helps to regulate the pressure inside the collection-extraction chamber. A preferred backpressure regulator is a 26-1700-type regulator, which is commercially available from Tescom, USA (Elk River, Minn.). The safety valve is preferably a standard commercially available valve and is interchangeable with other like valves that are known to those of ordinary skill in the art.

Methods

Figure 5:
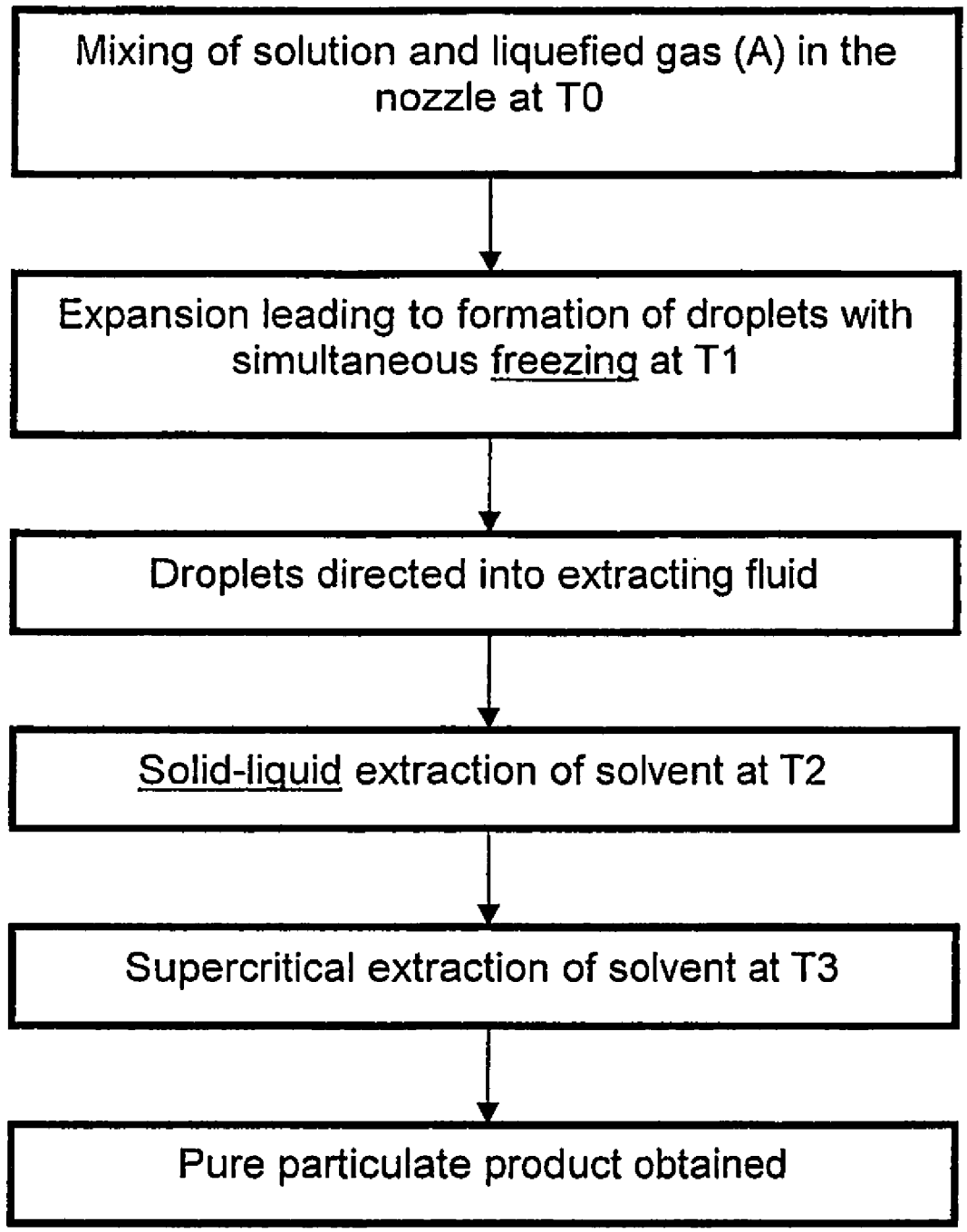
FIG. 5 is a flow chart showing the steps of a first embodiment of the method of the invention.

A flow chart of the steps involved in a first embodiment of the method of the invention is shown in FIG. 5. With reference thereto, the solution containing the solute to be precipitated is supplied to the nozzle and therein mixed with the first compressed or liquefied gas at temperature T0. The temperature T0 is selected to be high enough to avoid any blockages or clogging of the nozzle, and is typically between 0 and 100° C. Mixing between the solution and first compressed or liquefied gas usually leads to dissolution of portion of the gas in the solution. In general, mixing in the nozzle should be sufficiently fast to avoid any precipitation of the solute in the nozzle, which can produce clogging. At the end of the nozzle, the liquefied gas expands from an elevated pressure (typically between 30 and 300 atm) to a lower pressure, which is preferably closer to atmospheric (1 atm). This expansion occurs within the solution as well as outside the solution phase. Both expansion processes create fine droplets, which are controllably and reproducibly in the size range between 0.1 and 1000 µm, most preferably in the size range between 0.1 and 50 µm. Simultaneously, expansion of the gas causes a large Joules-Thomson effect which results in a rapid and uniform temperature decrease in the exiting spray stream.

In accordance with the first embodiment of the invention, the first temperature (T1) is below the freezing point of the solution. Therefore, the droplets formed upon expansion rapidly freeze into a solid state. These particles may be in the form of a composite of frozen solute and solvent zones, or in the form of a homogeneous solid mixture of frozen solute and solvent, or in the form of separate droplets of solute and solvent. Freezing occurs rapidly and almost simultaneously with the droplet dispersion because of the fast heat transfer between the expanding gas and small droplets. The frozen droplets are then contacted with the extracting fluid, which is kept at second temperature (T2) below the freezing point of the solution. Solid-liquid extraction then occurs, which consist of dissolution of the frozen solvent molecules in the extracting fluid. Fresh extracting fluid can be supplied and the solvent-saturated extracting fluid removed from the collection-extraction vessel, as shown in FIG. 1. The gas phase can also be removed using a separate outlet. When the solid-liquid extraction has been completed, pure compressed or liquefied gas can be supplied to the vessel and the temperature of the gas raised to a third temperature (T3), which is typically near or above the critical temperature of the gas. This step provides complete removal of both solvent and co-solvent from the chamber. The chamber is then depressurized and the particles are collected.

The size of the resulting particles depends, in large part, upon the spraying conditions. Thus, the size of the precipitated particles is closely related to the solution droplet size during spraying. A wide range of microparticles having different particle sizes can be made by varying the droplet size of the sprayed solution, which in turn can be varied by changing the nozzle geometry, solution temperature, solution flow rate, material composition and concentration in solution, choice of atomizing fluid, the presence, type and/or amount of processing aid (e.g., surfactant), and combinations thereof.

The particle size also depends on the extraction conditions. Extraction of the solvent from solid particles causes pores in the frozen particles. After solvent removal, such structure can collapse forming particles of a smaller size that the original droplet size. Thus, by varying the solution concentration, nanoparticles can be produced.

The freezing temperature may also have an effect on the size of pores in particles produced. Thus fast freezing may produces amorphous solid mixture or very small pores created by small solvent crystals whereas slower freezing rate may results on larger pores and even in a single hollow particle.

Figure 6:
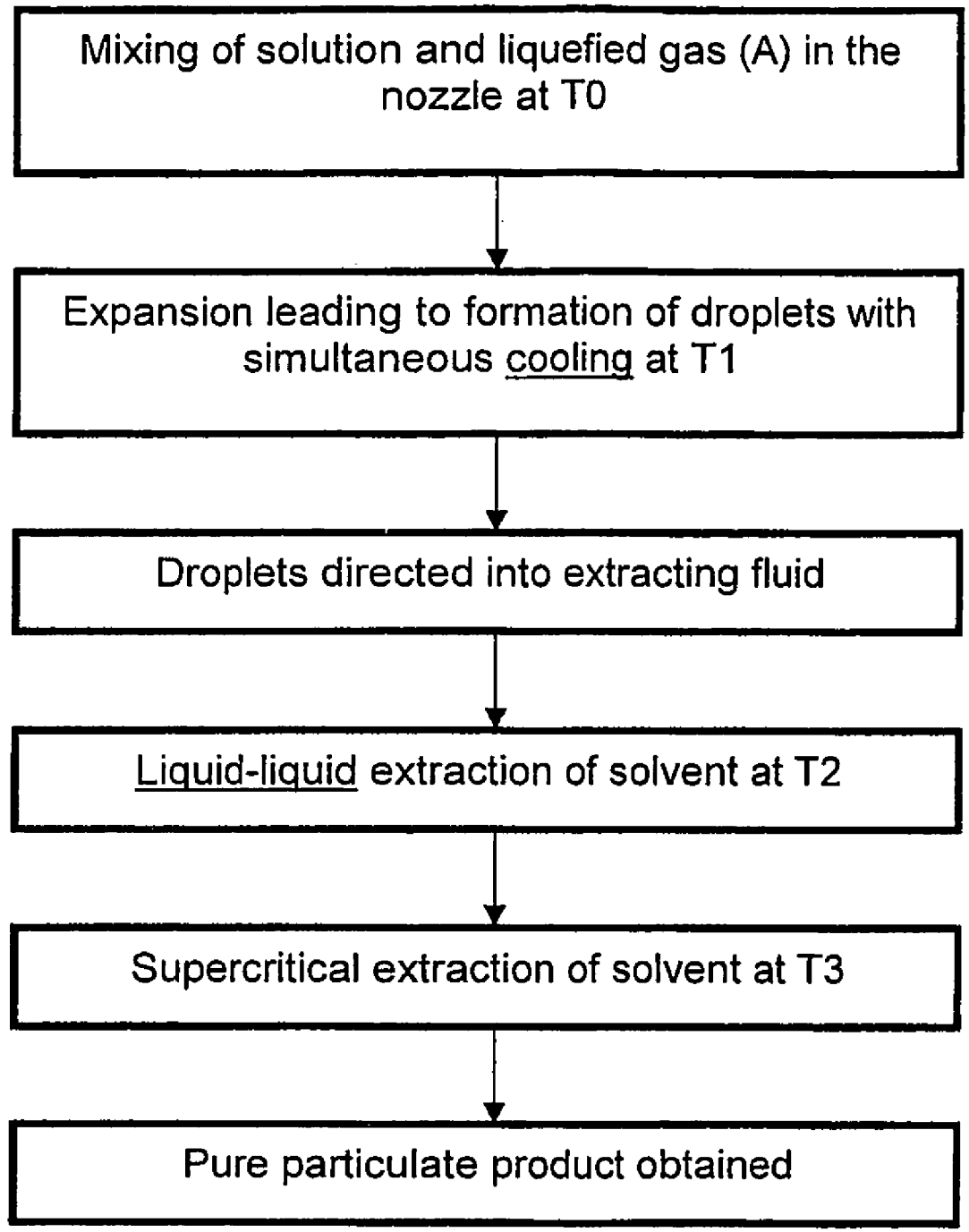
FIG. 6 is a flow chart showing the steps of a second embodiment of the method of the invention.

FIG. 6 shows a flow chart of the steps involved in a second embodiment of the invention. The difference between this embodiment and the first embodiment previously discussed is that the droplets exiting the nozzle are cooled in the expanding liquefied gas at a first temperature (T1) that is above the freezing point of the solution. The cooled droplets thus do not go into the solid state, but rather they may consist a super-cooled liquid solution. It will be appreciated that some phase separation may occur between the solute and solvent in the droplet. Liquid-liquid extraction then occurs once the droplets contact the extracting fluid. Extraction in this instance involves dissolution of the liquid solvent molecules in the liquid extracting fluid. The temperature of the gas extraction (T3) is also kept above the freezing point of the solution. Thus the droplets do not freeze and are dissolved in the antisolvent forming a continuous liquid phase. In this case, particles are precipitated due to a combined effect of temperature decrease (reduction of solute solubility) and the extraction of the solvent into extracting fluid.

Figure 7:
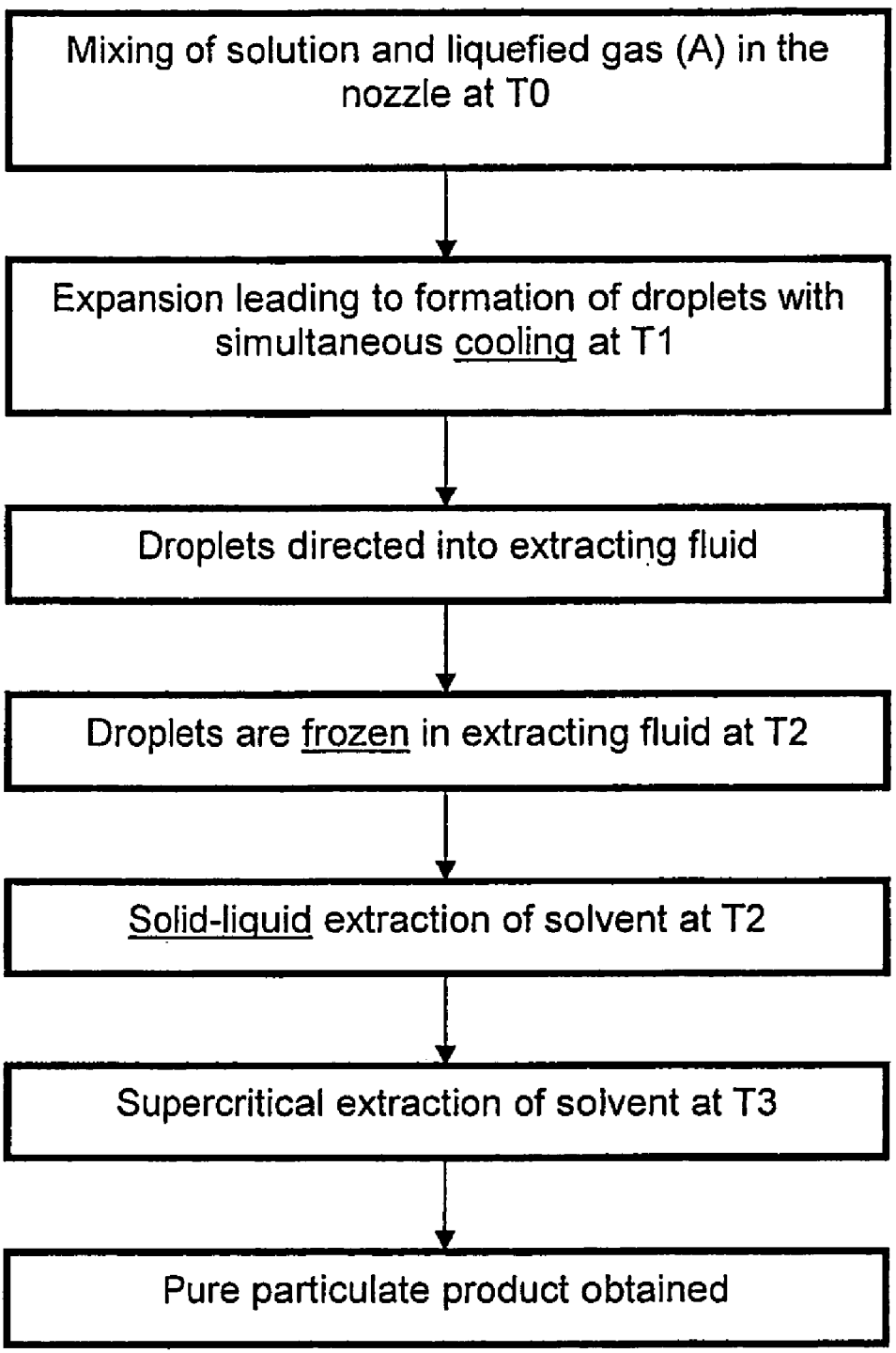
FIG. 7 is a flow chart showing the steps of a third embodiment of the method of the invention.

FIG. 7 shows a third embodiment of the method of the invention. In this embodiment, the first compressed or liquefied gas disperses and cools the solution into liquid droplets, which are then frozen when they contact the extracting fluid. The solvent is then removed by solid-liquid extraction as described in the first embodiment of the invention.

Figure 8:
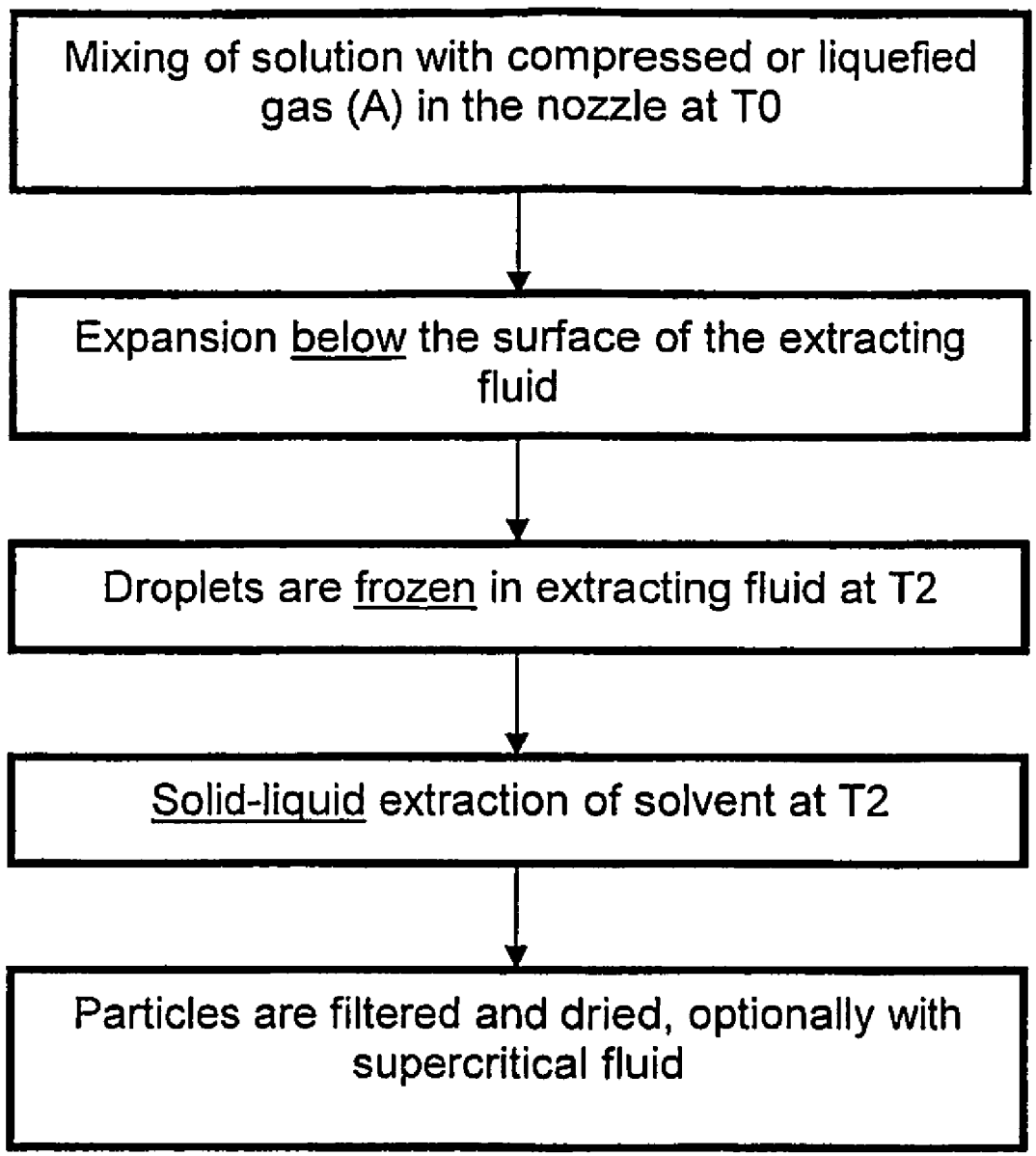
FIG. 8 is a flow chart showing the steps of a fourth embodiment of the method of the invention.

FIG. 8 shows a fourth embodiment of the method of the invention. In this embodiment, the first compressed or liquefied gas disperses and cools the solution into liquid phase droplets, which are injected below the surface level of the extracting fluid. Both the solution and the first compressed or liquefied gas are preferably heated prior to injection in order to prevent nozzle clogging. The bubbles created during expansion allow for more efficient mixing in the collection-extraction vessel. The solution droplets freeze upon contact with the extracting fluid. The solvent is then removed by solid-liquid extraction as described in the first embodiment of the invention.

Figure 9:
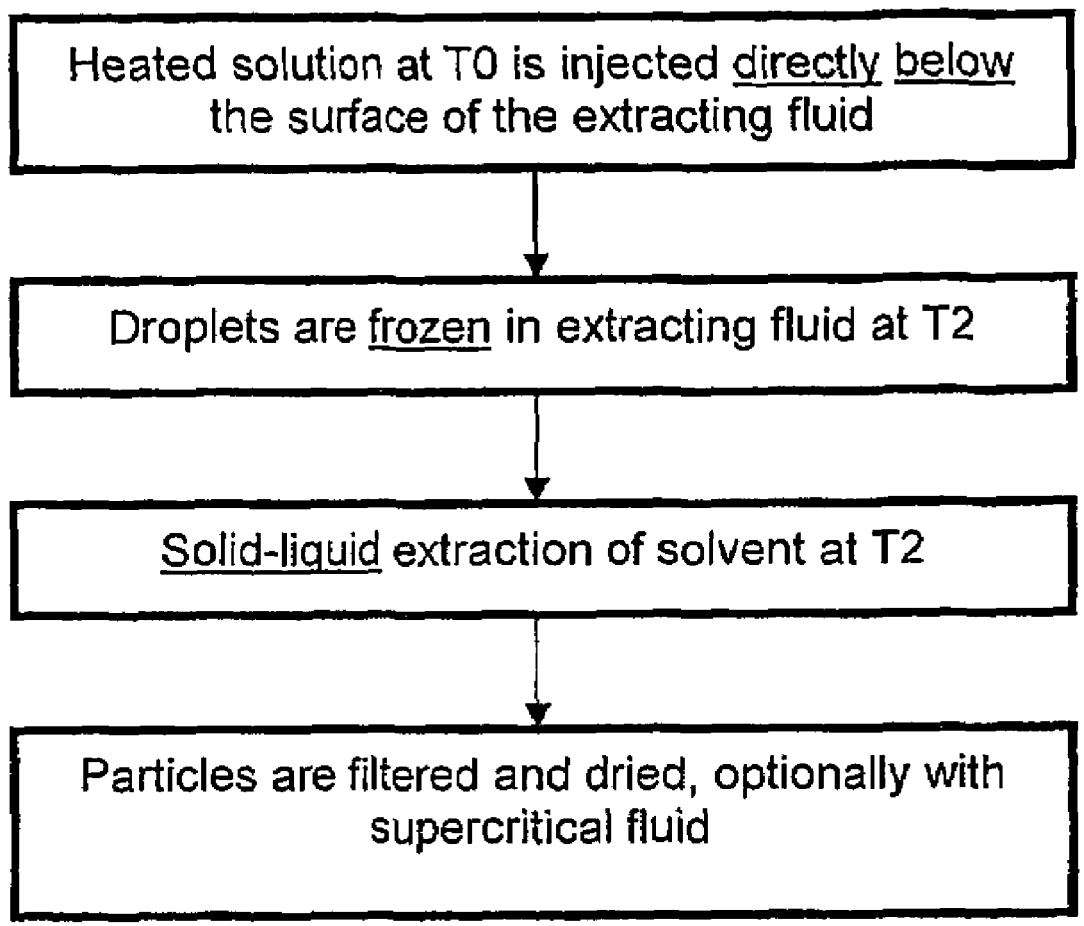
FIG. 9 is a flow chart showing the steps of a fifth embodiment of the method of the invention.

A fifth embodiment of the method of the invention is shown in FIG. 9. In this simplest method, a heated solution is injected directly below the surface of the extracting liquid. No compressed or liquefied gases are used for dispersion. Droplet formation results from jet break up of the solution, rather than fluid atomization. The solution droplets are frozen on contact with the extracting fluid. The solvent is then removed by solid-liquid extraction as described in the first embodiment of the invention. The resulting solid particles can be recovered from the extracting fluid by traditional techniques such as filtering and drying, or drying with supercritical fluid.

Figure 10:
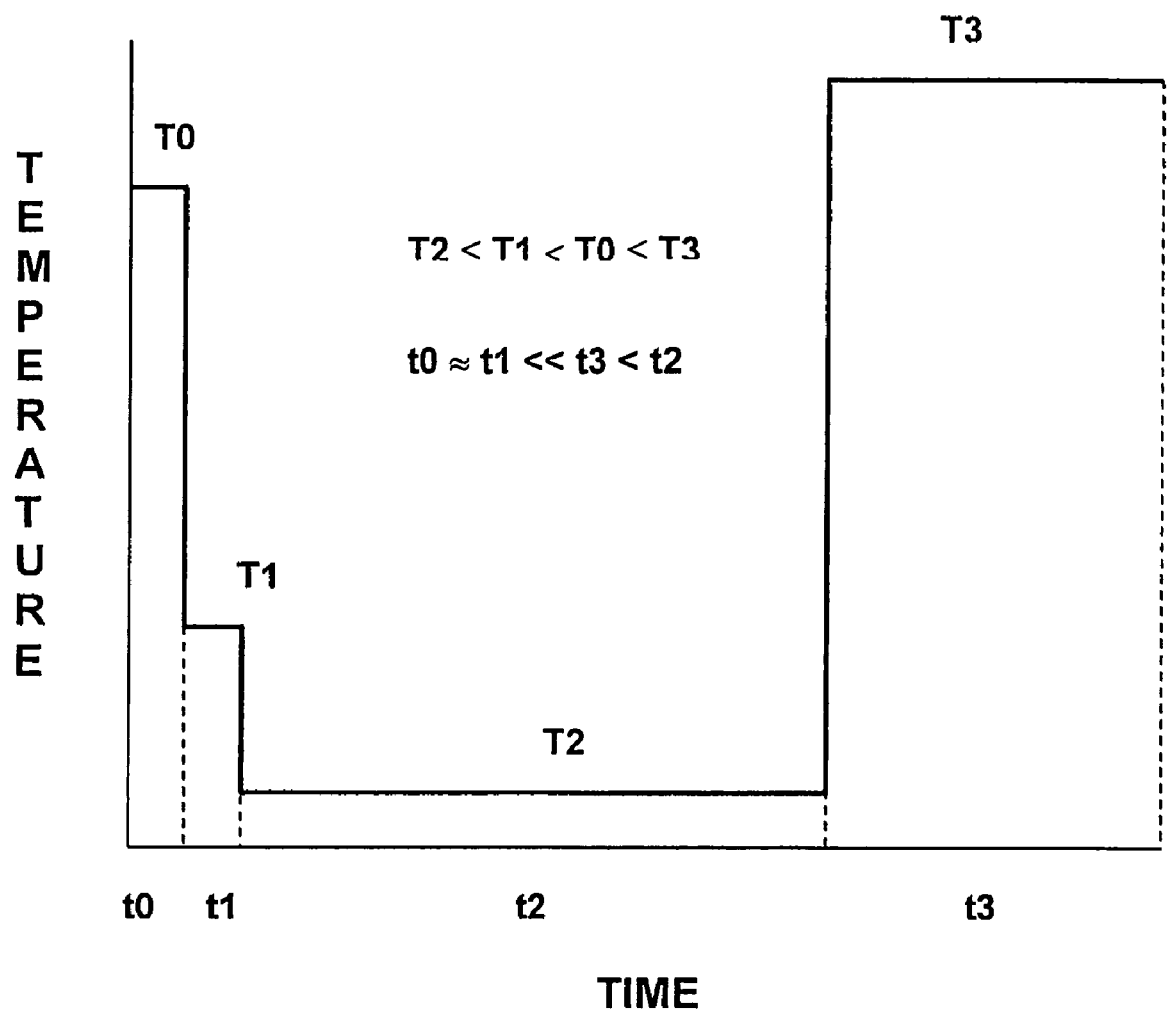
FIG. 10 is a graph showing temperature as a function of time during particle formation in accordance with the method of the invention.

FIG. 10 is a graph showing temperature as a function of time during the method of the invention. The process comprises the following stages: (a) solution injection at an initial temperature T0 for a period of time t0; (b) droplet dispersion and cooling or freezing at a first temperature T1 for a period of time t1; (c) solution freezing and/or solvent extraction by the extracting fluid at a second temperature T2 for a period of time t2; and (d) removal of all residual solvents at a third temperature T3 for a period of time t3 under supercritical or near-critical conditions.

The following examples are intended only to illustrate the invention and should not be construed as imposing limitations upon the claims.

EXAMPLE 1

Griseofulvin, a water insoluble drug, was formed into microparticles using the third embodiment of the method according to the invention. Generally speaking, solution droplets were frozen on contact with an extracting fluid, and then the solvent was removed from the solution by solid-liquid extraction to produce the particles.

Procedure:

Griseofulvin (GF) was dissolved in Dimethyl Sulfoxide (DMSO) at 5% weight/weight to form a solution. High-pressure nitrogen heated to 95° C. was used as the first compressed gas. The extracting fluid comprised a mixture $CO_2$, ethanol and water in approximately equal proportions. The extracting fluid was placed in an extraction vessel and was maintained at −23° C. Care was taken to ensure that the temperature of the extracting fluid was maintained significantly below the freezing point of DMSO (18° C.). The temperature of the extraction vessel was maintained constant using a cooling bath.

The first compressed gas (nitrogen) was mixed with the GF solution (flow rate 0.4 ml/min) in an impinging nozzle tee at a pressure of 150 bar. Both the solution and the atomizing gas were heated to 95° C. prior to being introduced into the mixing tee. The solution was sprayed (expanded to near atmospheric pressure) into the cooled extracting fluid through a 150-μm nozzle, resulting in the formation of droplets that froze upon contact with the extracting fluid. Solid-liquid extraction of the solvent (DMSO) from these frozen droplets resulted in the precipitation of GF as fine particles. When the solid-liquid extraction was completed, the solution was made to reach room temperature and the particles of GF were collected from the solution by filtration.

Figure 11:
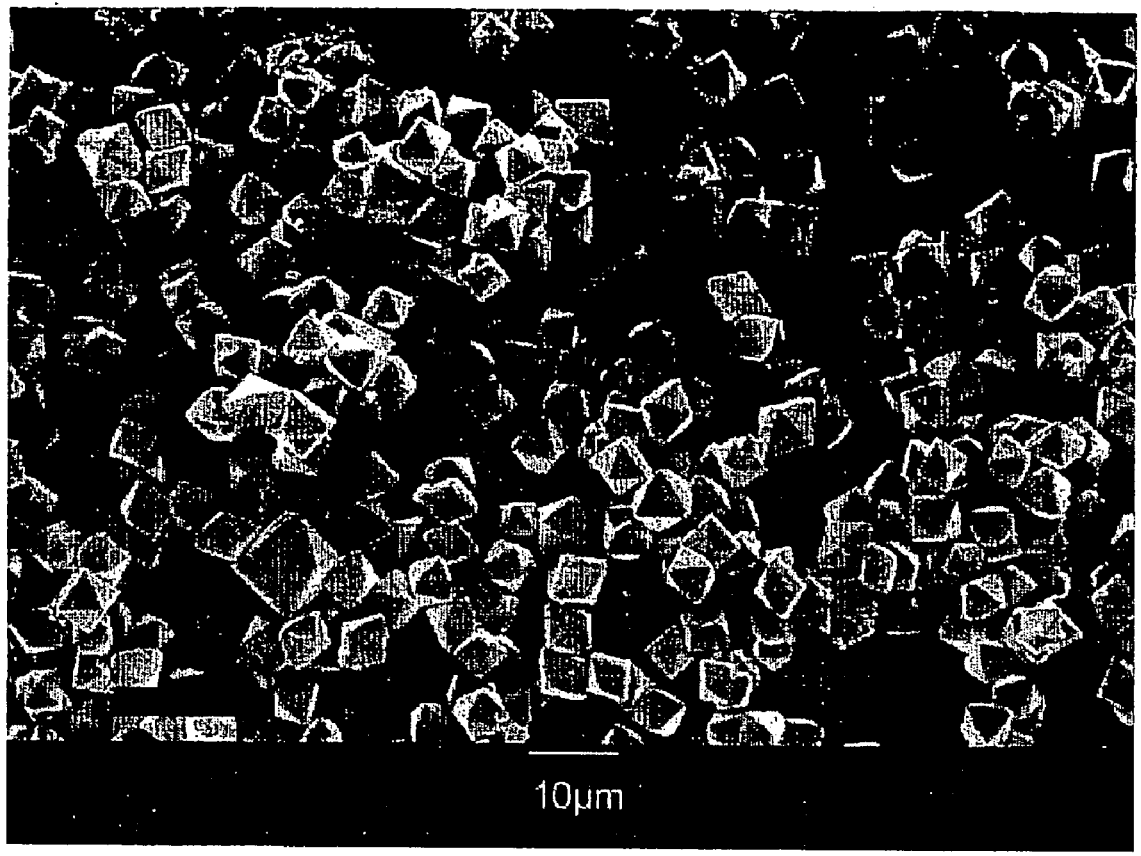
FIG. 11 is a scanning electron micrograph (SEM) showing particles produced in accordance with the method in Example 1.

Analysis:

The collected particles were analyzed using Scanning Electron Microscopy (SEM). The SEM micrograph of the particles is shown in FIG. 11. From FIG. 11 it is clear that the GF particles are in the form of non-agglomerated crystals, having an orthorhombic shape. The mean size of the substantially uniform particles is around 5–10 μm.

EXAMPLE 2

The following example illustrates the precipitation of lactose, a water-soluble sugar, in the form of porous microparticles using the third embodiment of the method of the invention. As in Example 1, droplets of solution were frozen upon contact with an extracting fluid. The solvent was then removed from the solution by solid-liquid extraction, resulting in the production of particles.

Procedure:

Lactose was dissolved in water at 7% weight/weight to form a solution. Particle precipitation experiments were carried out in the same manner and under the same extraction conditions as described in Example 1. The extraction solution was again a mixture of $CO_2$, ethanol and water in equal proportions. The flow rate of the lactose solution was 1 ml/min and was introduced after being mixed with the atomizing heated nitrogen gas (75 bar) in the low dead volume tee through a 150-μm nozzle.

Porous lactose particles were formed by solid-liquid extraction of water from the frozen solution droplets. When the solid-liquid extraction was completed the solution was made to reach room temperature and the particles of lactose were collected from the solution by filtration.

Figure 12:
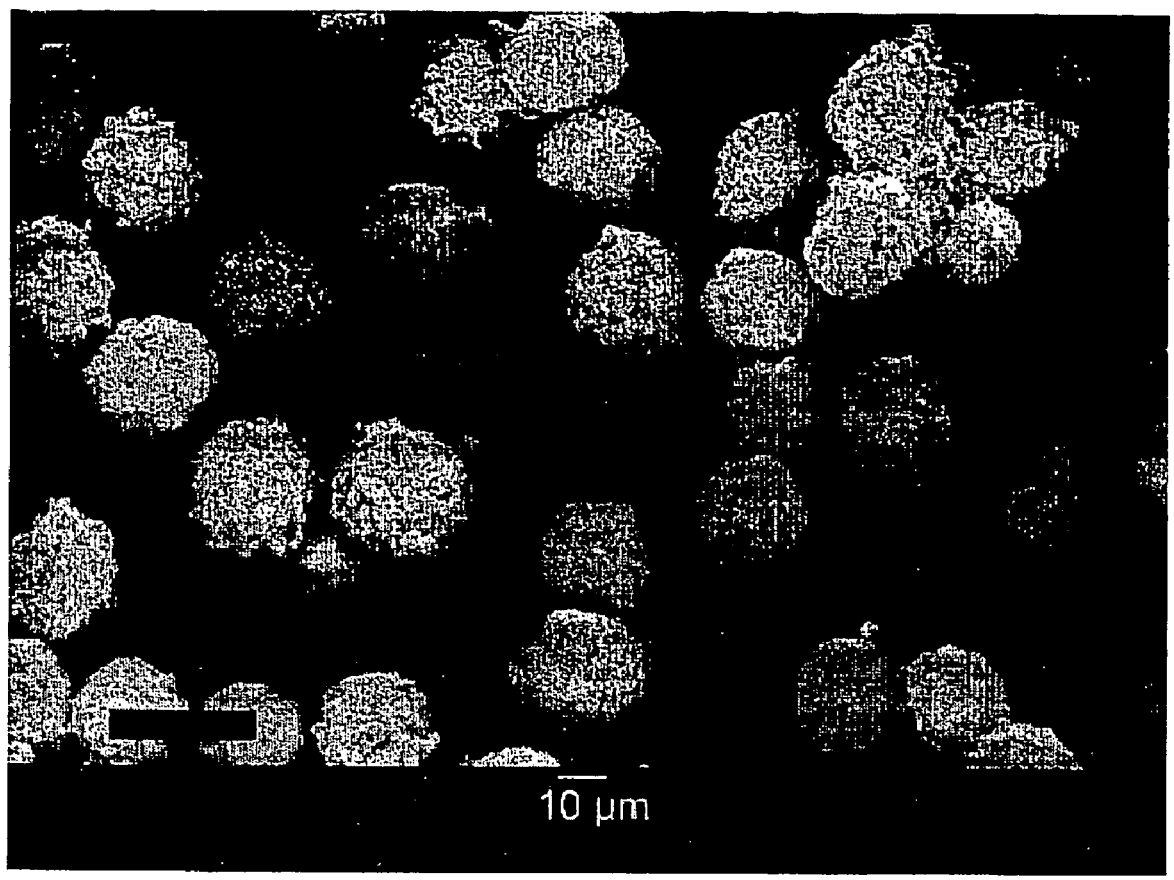
FIG. 12 is an SEM showing particles prepared in accordance with the method in Example 2.

Analysis:

Analysis of the porous lactose particles was carried out in the same manner as described in Example 1. FIG. 12 is an SEM micrograph of the lactose particles. The SEM micrograph shows that the porous lactose particles are spherical in shape and have a substantially uniform mean size of about 20–30 μm. Close examination of the individual porous lactose particles revealed that they are made up of tiny individual lactose crystals having sizes in the nanometer range. If desired, these lactose nanocrystals can be obtained simply by crumbling the large porous lactose spheres.

Additional advantages and modifications will readily occur to those skilled in the art. Therefore, the invention in its broader aspects is not limited to the specific details and illustrative examples shown and described herein. Accordingly, various modifications may be made without departing from the spirit or scope of the general inventive concept as defined by the appended claims and their equivalents.

What is claimed is:

1. A method of forming particles comprising:
   providing a solution comprising a solute dispersed or dissolved in a solvent;
   contacting the solution with a first compressed or liquefied gas at an initial temperature to form a mixture;
   expanding the mixture at a first temperature to form droplets;
   contacting the droplets with an extracting fluid at a second temperature at which the solvent is extracted from the droplets to form particles comprising the solute; and
   separating the particles from the extracting fluid and solvent.

2. The method according to claim 1 wherein the extracting fluid comprises a homogeneous blend of a second compressed or liquefied gas and a co-solvent.

3. The method according to claim 1 wherein the first temperature is below the freezing point of the solution thereby forming droplets that are in a solid state when the droplets contact the extracting fluid.

4. The method according to claim 1 wherein the first temperature is above the freezing point of the solution thereby forming droplets that are in a liquid state when the droplets contact the extracting fluid.

5. The method according to claim 4 wherein the droplets freeze upon contacting the extracting fluid.

6. The method according to claim 1 wherein the droplets are injected subsurface into the extracting fluid.

7. The method according to claim 1 further comprising removing the extracting fluid and solvent from the particles by contacting the same with a supercritical fluid at a third temperature.

8. The method according to claim 1 wherein the solute is a biologically active agent selected from the group consisting of proteins, monoclonal antibodies, peptides, nucleic acids, polysaccharides, steroids, antibiotics, anesthetics, sedatives, cardiovascular agents, anti-tumor agents, vitamins, organic and inorganic drugs, and diagnostic agents.

9. The method according to claim 1 wherein the solution further comprises an excipient selected from the group consisting of sugars, salts, buffers, stabilizers, surfactants, amino-acids, bulking agents, dispersion and release enhancing agents.

10. The method according to claim 1 wherein the solution further comprises a polymer selected from the group consisting of biodegradable polymers, biocompatible polymers and lipids.

11. The method according to claim 1 wherein the particles have a mean diameter within the range of from about 0.05 to 1000 μm.

12. The method according to claim 1 wherein the particles have a mean diameter within the range of from about 0.5 to 5 μm and are suitable for use in respiratory applications.

13. The method according to claim 1 wherein the particles have a mean diameter within the range of from about 0.05 to 1 μm and are suitable for use in nano-formulations.

14. The method according to claim 2 wherein the weight ratio of the second compressed or liquefied gas to the co-solvent in the extracting fluid is adjusted within the range of from about 0:100 to about 100:0, depending on the required extraction temperature and miscibility between liquefied gas and co-solvents.

15. The method according to claim 1 wherein the second compressed or liquefied gas in extracting fluid is selected from the group consisting of carbon dioxide, propane, ethane, nitrogen oxide, ammonia, and hydrofluorocarbons.

16. The method according to claim 1 wherein the first compressed or liquefied gas is selected from the group consisting carbon dioxide, propane, ethane, nitrogen oxide, ammonia, and hydrofluorocarbons.

17. The method according to claim 1 wherein the first compressed or liquefied gas is selected from the group consisting of air, nitrogen, argon and xenon.

18. The method according to claim 1 wherein the solution and the first compressed or liquefied gas are mixed together in a nozzle.

19. The method according to claim 1 wherein the solvent is selected from the group consisting of ethanol, alcohol group, acetone, pentane, isopentane, ethyl acetate, methylene chloride, chloroform, dimethyl sulfoxide (DMSO), dimethyl formamide (DMF), tetrahydrofuran (THF), water, and combinations thereof.

20. A method of forming particles comprising:
  providing a solution comprising a solute dispersed or dissolved in a solvent;

injecting the solution subsurface into an extracting fluid at a rate sufficient to cause the injected solution to form droplets within the extracting fluid;

extracting the solvent from the droplets to form particles comprising the solute; and separating the particles from the extracting fluid and solvent.

* * * * *